United States Patent [19]

Allen et al.

[11] 4,425,342
[45] Jan. 10, 1984

[54] 1-(SUBSTITUTED) PIPERAZINE-4-BENZENESULFINAMIDES, COMPOSITIONS AND METHOD OF USE

[75] Inventors: Richard C. Allen; Solomon S. Klioze, both of Flemington, N.J.

[73] Assignee: Hoechst-Roussel Pharmaceuticals, Somerville, N.J.

[21] Appl. No.: 24,930

[22] Filed: Mar. 29, 1979

[51] Int. Cl.³ .................. A61K 31/495; C07D 295/00; C07D 401/12
[52] U.S. Cl. .................................... 424/250; 544/360; 544/383
[58] Field of Search ................. 544/360, 383; 424/250

[56] References Cited

U.S. PATENT DOCUMENTS

| | | | |
|---|---|---|---|
| 3,464,971 | 9/1969 | Weaver et al. | 544/383 |
| 3,506,649 | 4/1970 | Wei et al. | 544/383 |
| 3,980,787 | 9/1976 | Klioze et al. | 424/267 |
| 4,015,004 | 3/1977 | Klioze et al. | 544/383 |

OTHER PUBLICATIONS

Wolff, *Burger's Medicinal Chemistry*, 4th Ed., Part I, The Basis of Medicinal Chemistry, pp. 108–111, 169–171.

Burger, *Medicinal Chemistry*, Third Ed., Part I, pp. 50–53.

S. S. Klioze et al., J. Med. Chem. 21, 400, 1978.

*Primary Examiner*—Mary C. Lee
*Assistant Examiner*—James H. Turnipseed
*Attorney, Agent, or Firm*—Raymond R. Wittekind

[57] ABSTRACT

Benzenesulfinamides of the formula

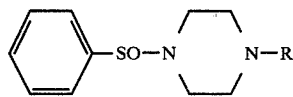

wherein R is pyridyl, phenyl or phenyl substituted by halogen, loweralkyl, loweralkoxy or trifluoromethyl and the pharmaceutically acceptable acid addition salts thereof are useful blood pressure reducing agents.

23 Claims, No Drawings

1-(SUBSTITUTED) PIPERAZINE-4-BENZENESULFINAMIDES, COMPOSITIONS AND METHOD OF USE

The present invention relates to benzenesulfinamides. More particularly, the present invention relates to benzenesulfinamides of the formula 1

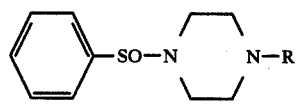

wherein R is pyridyl, phenyl or phenyl substituted by halogen, loweralkyl, loweralkoxy or trifluoromethyl and the pharmaceutically acceptable acid addition salts thereof, which are useful as blood pressure reducing agents, i.e., as antihypertensives, either alone or in combination with inert blood pressure reducing adjuvants.

As used throughout the specification and appended claims, the term "alkyl" refers to a straight or branched chain hydrocarbon containing no unsaturation and having 1 to 20 carbon atoms such as methyl, ethyl, 1-propyl, 2-propyl, 1,1-dimethylethyl, 3-hexyl, 2-octyl, 1-decyl and so forth; the term "alkoxy" refers to a monovalent substituent which consists of an alkyl group linked through an ether oxygen having its free valence bond from the ether oxygen such as methoxy, ethoxy, 1-propoxy, 2-propoxy, 1,1-dimethylethoxy, 3-hexoxy, 2-octoxy, 1-decoxy and so forth; the term "halogen" refers to a member of the family consisting of fluorine, chlorine, bromine and iodine. The term "lower" applied to any of the aforementioned groups refers to a group having a carbon skeleton containing 1 to 10 carbon atoms, inclusive.

The novel benzenesulfinamides of the present invention are prepared by sulfinylation of N-substituted piperazines of formula 2

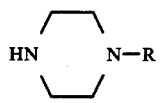

wherein R is as above by means of a phenylsulfinyl halide of formula 3

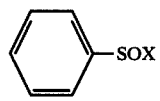

wherein X is bromo or chloro.

The N-substituted piperazine starting materials of formula 2 are prepared by methods described in U.S. Pat. No. 4,015,044, issued to S. S. Klioze and R. C. Allen on Mar. 29, 1977.

The sulfinylation is conveniently performed by dissolving or suspending the piperazine 2 in an inert solvent containing an acid acceptor and adding the phenylsulfinyl halide 3. Suitable inert solvents include, among others, halocarbons such as dichloromethane, trichloromethane and tetrachloromethane, aromatic hydrocarbons such as benzene, toluene and xylene and ethers such as diethylether and tetrahydrofuran. Suitable acid acceptors include organic tertiary amine bases, both aliphatic and heterocyclic, such as, for example, triethylamine, tripropylamine, pyridine, picoline, lutidine, collidine, quinoline, 1,5-diazabicyclo[5.4.0]-undec-5-ene and the like. Dichloromethane and triethylamine are the preferred solvent and acid acceptor, respectively. The reaction temperature is not narrowly critical. However, it is preferable to perform the reaction at a temperature within the range of from about room temperature to about the boiling point of the reaction mixture to promote a reasonable rate of reaction. The sulfinylation is suitably performed using about molar-equivalents of piperazine 2, benzenesulfinyl halide 3 and acceptor. However, slight molar excesses of the halide 3 and acceptor may be employed, also to promote the rate of reaction.

The benzenesulfinamides of the present invention are useful as antihypertensive agents due to their ability to depress blood pressure in mammals. Antihypertensive activity is measured in the spontaneous hypertensive rat by the indirect tail cuff method described in "Methods in Pharmacology," A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activities of some of the compounds, expressed as mm decrease in mean arterial blood pressure, are given in Table I.

TABLE I

| Compound | Dose (mg/kg of body weight) | mm/Hg |
|---|---|---|
| 1-phenylpiperazine-4-benzenesulfinamide | 10 | −22 |
|  | 25 | −42 |
|  | 50 | −83 |
| 1-(2-pyridyl)piperazine-4-benzenesulfinamide | 10 | −36 |
|  | 25 | −59 |
|  | 50 | −80 |

Examples of other compounds of the invention include:
1-(4-propylphenyl)piperazine-4-benzenesulfinamide;
1-(3-ethoxyphenyl)piperazine-4-benzenesulfinamide; and
1-(4-fluorophenyl)piperazine-4-benzenesulfinamide.

1-(phenyl)- and 1-(pyridyl)piperazine-4-benzenesulfinamides are the preferred antihypertensives of the present invention.

Blood pressure reduction is achieved when the benzenesulfinamides are administered to a subject requiring such treatment at an effective oral, parenteral or intravenous dose of from 1 to 50 mg/kg of body weight per day. A preferred effective dose within this range is from about 15 to 35 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compounds. It is to be further understood that the dosages set forth herein are examples only and that they do not, to any extent, limit the scope or practice of the invention.

Effective amounts of the benzenesulfinamides of the present invention may be administered to a subject by one of various methods, for example, orally as in capsules or tablets, parenterally in the form of sterile solutions or suspensions, and in some cases intravenously in the form of sterile solutions. The benzenesulfinamides, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The benzenesulfinamides of the present invention may be administered orally, for example, with an inert diluent or with an edible carrier. They may be enclosed in gelatin capsules or compressed into tablets. For the purpose or oral therapeutic administration, the aforesaid compounds may be incorporated with excipients and used in the form of tablets, troches, capsules, elixirs, suspensions, syrups, wafers, chewing gums and the like. These preparations should contain at least 0.5% of the benzenesulfinamide, the active ingredient, but may be vared depending upon the particular form and may conveniently be between 4% to about 70% of the weight of the unit. The amount of present compound in such compositions is such that a suitable dosage will be obtained. Preferred compositions and preparations according to the present invention are prepared so that an oral dosage unit form contains between 1.0–300 milligrams of the benzenesulfinamides.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present benzenesulfinamides, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the benzenesulfinamides of the present invention may be incorporated into a solution or suspension. These preparations should contain at least 0.1% of the aforesaid compound, but may be varied to be between 0.5 and about 50% of the weight thereof. The amount of the present compound in such compositions is such that a suitable dosage will be obtained. Preferred compositions and preparations according to the present invention are prepared so that a parenteral dosage unit contains between 0.5 to 100 milligrams of the benzo[b]thiophene.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1

To a solution of 4.87 g of N-phenylpiperazine in 150 ml of dichloromethane containing 4.59 ml of triethylamine is added dropwise with stirring under nitrogen a solution of 4.82 g of benzenesulfinyl chloride in 50 ml of dichloromethane. The reaction mixture is stirred for 3 hours at room temperature, diluted with 100 ml of dichloromethane and washed with 150 ml of water and 100 ml of 5% potassium carbonate solution. The organic layer is dried over anhydrous sodium sulfate and evaporated in vacuo to a nearly colorless crystalline solid. Recrystallization from ethanol affords 6.37 g of 1-phenylpiperazine-4-benzenesulfinamide as a nearly colorless crystalline solid, mp, 101°–104° (softens 98°).

Analysis: Calculated for $C_{16}H_{18}N_2OS$: 67.10% C; 6.34% H; 9.78% N. Found: 66.86% C; 6.42% H; 9.68% N.

EXAMPLE 2

To a solution of 4.90 g of 1-(2-pyridyl)piperazine in 150 ml of dichloromethane containing 4.59 ml of triethylamine is added dropwise with stirring under nitrogen a solution of 4.82 g of benzenesulfinyl chloride in 50 ml of dichloromethane. The reaction mixture is stirred for 3 hours at room temperature, diluted with 100 ml of dichloromethane, and washed with 150 ml water and 100 ml 5% potassium carbonate. The organic layer is dried over sodium sulfate and evaporated in vacuo to give a yellow crystalline solid. Recrystallization from ethanol affords 4.14 g of 1-(2-pyridyl)piperazine-4-benzenesulfinamide as a colorless crystalline solid, mp 83°–86° (soften 81°). A second crop (1.24 g) is obtained by concentration of the mother liquors, total yield: 5.38 g.

Analysis: Calculated for $C_{15}H_{17}N_3OS$: 62.69% C; 5.96% H; 14.62% N. Found: 62.61% C; 6.03% H; 14.57% N.

The following benzenesulfinamides may be prepared from the appropriate N-substituted piperazines by employing the procedure described in either Example 1 or 2:

1-(4-methoxyphenyl)piperazine-4-benzenesulfinamide;
1-(3-chlorophenyl)piperazine-4-benzenesulfinamide;
1-(2-methylphenyl)piperazine-4-benzenesulfinamide;
1-(3-methoxyphenyl)piperazine-4-benzenesulfinamide;
1-(2-chlorophenyl)piperazine-4-benzenesulfinamide;
1-(2-methoxyphenyl)piperazine-4-benzenesulfinamide;
1-(3-trifluoromethylphenyl)piperazine-4-benzenesulfinamide; and
1-(3-methylphenyl)piperazine-4-benzenesulfinamide.

We claim:

1. A compound of the formula

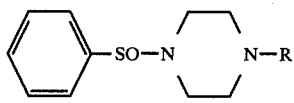

wherein R is pyridyl, phenyl or phenyl substituted by halogen, loweralkyl, loweralkoxy or trifluoromethyl and the pharmaceutically acceptable acid addition salts thereof.

2. The compound of claim 1 wherein R is pyridyl.

3. The compound of claim 2 which is 1-(2-pyridyl)-piperazine-4-benzenesulfinamide.

4. The compound of claim 1 which is 1-phenylpiperazine-4-benzenesulfinamide.

5. The compound of claim 1 which is 1-(4-methoxyphenyl)piperazine-4-benzenesulfinamide.

6. The compound of claim 1 which is 1-(3-chlorophenyl)-piperazine-4-benzenesulfinamide.

7. The compound of claim 1 which is 1-(2-methylphenyl)-piperazine-4-benzenesulfinamide.

8. The compound of claim 1 which is 1-(3-methoxyphenyl)-piperazine-4-benzenesulfinamide.

9. The compound of claim 1 which is 1-(2-chlorophenyl)-piperazine-4-benzenesulfinamide.

10. The compound of claim 1 which is 1-(2-methoxyphenyl)-piperazine-4-benzenesulfinamide.

11. The compound of claim 1 which is 1-(3-trifluoromethyl)-phenyl)piperazine-4-benzenesulfinamide.

12. The compound of claim 1 which is 1-(3-methylphenyl)-piperazine-4-benzenesulfinamide.

13. The compound of claim 1 which is 1-(4-propylphenyl)-piperazine-4-benzenesulfinamide.

14. The compound of claim 1 which is 1-(3-ethoxyphenyl)-piperazine-4-benzenesulfinamide.

15. The compound of claim 1 which is 1-(4-fluorophenyl)-piperazine-4-benzenesulfinamide.

16. A method of reducing blood pressure in mammals comprising administering to a mammal requiring blood pressure reduction a blood pressure reducing effective amount of a compound of the formula

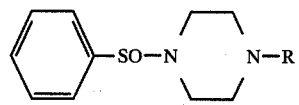

wherein R is pyridyl, phenyl or phenyl substituted by halogen, loweralkyl, loweralkoxy or trifluoromethyl and the pharmaceutically acceptable acid addition salts thereof.

17. The method of claim 16 wherein R is pyridyl.

18. The method of claim 17 wherein the compound is 1-(2-pyridyl)piperazine-4-benzenesulfinamide.

19. The method of claim 16 wherein the compound is 1-phenylpiperazine-4-benzenesulfinamide.

20. A blood pressure reducing composition comprising an inert blood pressure reducing adjuvant and as the active ingredient, an amount effective in reducing blood pressure of a compound of the formula

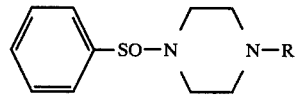

wherein R is pyridyl, phenyl or phenyl substituted by halogen, loweralkyl, loweralkoxy or trifluoromethyl.

21. The composition of claim 20 wherein R is pyridyl.

22. The composition of claim 21 wherein the compound is 1-(2-pyridyl)piperazine-4-benzenesulfinamide.

23. The composition of claim 20 wherein the compound is 1-phenylpiperazine-4-benzenesulfinamide.

* * * * *